US008011973B2

(12) United States Patent
Feng et al.

(10) Patent No.: US 8,011,973 B2
(45) Date of Patent: Sep. 6, 2011

(54) CONNECTOR AND A METHOD OF MANUFACTURING THE SAME

(75) Inventors: Jiang Feng, Shenzhen (CN); Wang Zhenbo, Shenzhen (CN); Zhang Zifeng, Shenzhen (CN); Wang Kun, Shenzhen (CN); Huang Zhixue, Shenzhen (CN)

(73) Assignee: BYD Company Ltd., Shenzhen (CN)

( * ) Notice: Subject to any disclaimer, the term of this patent is extended or adjusted under 35 U.S.C. 154(b) by 243 days.

(21) Appl. No.: 12/346,753

(22) Filed: Dec. 30, 2008

(65) Prior Publication Data

US 2010/0015857 A1   Jan. 21, 2010

(30) Foreign Application Priority Data

Jul. 18, 2008   (CN) ...................... 2008 2 0095657 U
Jul. 25, 2008   (CN) .......................... 2008 1 0142658
Jul. 25, 2008   (CN) ...................... 2008 2 0095923 U (51) Int. Cl.
*H01R 24/00* (2006.01)

(52) U.S. Cl. ....................................................... 439/676

(58) Field of Classification Search .................. 439/676, 439/427, 843–847, 827, 891, 851–854; 29/876, 29/874, 837, 825, 747
See application file for complete search history.

(56) References Cited

U.S. PATENT DOCUMENTS

| 4,087,152 | A  | * | 5/1978  | Kolm ............................. 439/827 |
| 5,013,264 | A  | * | 5/1991  | Tondreault .................... 439/636 |
| 5,203,813 | A  | * | 4/1993  | Fitzsimmons et al. .......... 29/876 |
| 7,347,746 | B1 | * | 3/2008  | He ................................. 439/843 |
| 2007/0269996 | A1 | * | 11/2007 | Chia ................................ 439/66 |

* cited by examiner

*Primary Examiner* — Edwin A. Leon
(74) *Attorney, Agent, or Firm* — Morgan, Lewis & Bockius LLP (57) ABSTRACT

The invention discloses a connector that comprises an insulation body and one or more conductive terminals within the insulation body. The one or more conductive terminals comprise at least one clamping portion to clamp onto the insulation body. The invention further discloses an endoscope, which comprises a telescope, an imaging means, an image sensor that transforms optical signals from the imaging means into electrical signals and a PCB board that organizes and outputs the electrical signals, the imaging means, image sensor and PCB board being located in the telescope, wherein the endoscope further comprises the connector that electrically connects the image sensor and the PCB board to form a first assembly. The invention further discloses a method to make the connector.

14 Claims, 9 Drawing Sheets

CONNECTOR AND A METHOD OF MANUFACTURING THE SAME

RELATED APPLICATIONS

This application claims priority to Chinese Patent Application No. 200810142658.0, "A Connector and a manufacturing method of the same," filed on Jul. 25, 2008, which is hereby incorporated by reference in its entirety.

This application claims priority to Chinese Patent Application No. 200820095923.X, "A connector and an endoscope comprises the same," filed on Jul. 25, 2008, which is hereby incorporated by reference in its entirety.

This application claims priority to Chinese Patent Application No. 200820095657.0, "A new-style connector," filed on Jul. 18, 2008, which is hereby incorporated by reference in its entirety.

This application relates to U.S. patent application, "An endoscope and a method of manufacturing the same," filed on Dec. 30, 2008 (Ser. No. 12/346,745), which is hereby incorporated by reference in its entirety.

FIELD OF THE INVENTION

The invention relates to an endoscope, a method of manufacturing the same, and a connector for use in an endoscope.

BACKGROUND OF THE INVENTION

An electrical connector having multiple cable lines can be used to electrically connect electrical equipment. In the field of medical devices, an endoscope is connected to an external video processor by such an electrical connector. The endoscope usually comprises a solid image collection element that is inserted into the body. The video processor generates endoscope image signals by processing the signals received from the solid image collection element. The electrical connector includes multiple cable lines for sending and receiving signals, providing driving power, and transmitting signals produced by the endoscope lens and an image sensor.

The traditional connector includes an insulation body and electrical terminals set within the insulation body. The traditional connector has relatively a large size and it is assembled by inserting the terminals into the body. However, this is connector is unreliable because the terminals are not stably fixed into the body. The connector in the endoscope often requires a time-consuming assembly method to fit in the small space within the endoscope, which could result in inferior product quality.

Chinese Invention Patent No. CN101102714, entitled "An electrical connector of endoscope, an endoscope and an assembly method of the same," discloses an electrical connector for use in an endoscope, an endoscope and an assembly method of electrical connector. As disclosed in the patent, the endoscope comprises an insertion part, an operation part at an end of the insertion part, a cable connected to the operation part, and an electrical connector. A signal line passes through the endoscope and extends from the electrical connector to the other end. The signal line consists of a cable line and a connector that can detachably connect to an end of the cable line. However, since the terminals of the connector are set within the connector, this connection may be unstable and cause poor signal transmission.

SUMMARY

The invention discloses a connector of simple structure for the precise positioning of various parts within an endoscope. Further, the invention provides a simple and economic way of manufacturing the connector.

Further, the invention provides an endoscope of simple structure using the connector provided by the invention to precisely position the parts within the telescope.

According to some embodiments of the invention, a connector comprises an insulation body and one or more conductive terminals within the insulation body, wherein the one or more conductive terminals comprise at least one clamping portion to clamp onto the insulation body.

In some embodiments, the clamping portion is configured to be a projection by bending a side edge of the one or more terminals. In some embodiments, a conductive terminal comprises two or more clamping portions, and their bending directions are different from each other. In some embodiments, the conductive terminal comprises two symmetric clamping portions. In some embodiments, the conductive terminal comprises a body, a contacting part extending from one end of the body, and a welding part extending from the other end of the body to configure a bending portion. In some embodiments, the clamping portions are formed on the body.

In some embodiments, a pad is formed on the welding part.

In some embodiments, guiding grooves are formed on the pad.

In some embodiments, the insulation body is configured to be a column.

In some embodiments, wherein, the insulation body comprises a body portion and a connection portion connecting to the body portion.

In some embodiments, at least one projection is formed on the insulation body.

In some embodiments, the conductive terminals have longitudinal axis parallel to the longitudinal axis of the at least one projection.

In some embodiments, the clamping portion is configured to include a head portion and a foot portion, the head portion has an upper end exposed out of the end face of the insulation body and form an engagement face with the end face, the foot portion is formed by bending the extension of the head portion and extends out of the other end face of the insulation body, and the foot portion extends to form an extension portion for connecting the terminal to the body.

In some embodiments, the extension portion is symmetric.

In some embodiments, a welding pad is configured to connect to the head portion.

In some embodiments, the insulation body has at least one guiding groove formed on the pad.

In some embodiments, the insulation body is configured to be a column.

In some embodiments, at least one projection is formed on the insulation body.

In some embodiments, the conductive terminals have longitudinal axis parallel to the longitudinal axis of the at least one projection.

Further, the invention provides a method to manufacture the connector according to the invention, including the following steps of:

pressing the material belt to form a conductive terminal;

bending and extending an end of the conductive terminal to form a clamping portion; and putting at least one of the conductive terminals so obtained in position within a mould, then folding the mould and insert molding to form a connector having an insulation body and conductive terminals.

In some embodiments, in the step of pressing the material belt to form a conductive terminal, two or more clamping portions having different bending directions are formed.

Further, the invention provides an endoscope, which comprises a telescope, an imaging means, an image sensor that transforms optical signals from the imaging means into electrical signals and a PCB board that organizes and outputs the electrical signals, the imaging means, image sensor and PCB board being located in the telescope, wherein the endoscope further comprises the connector that electrically connects the image sensor and the PCB board to form a first assembly.

In some embodiments, the imaging means comprises a group of lenses.

In some embodiments, optical fiber is set in the telescope.

In some embodiments, the endoscope further comprises a bracket, one end of which connects to the output end of the imagine means to form a second assembly and the other end connects to the first assembly so as to integrate the first and second assemblies.

In some embodiments, the bracket is configured to be a tubular shape, with one end being fixed around the first assembly and the other end being fixed around the output end of the imaging means.

In some embodiments, a coupled operating configuration is respectively arranged on the outer wall of the connector and the inner wall of the bracket.

In some embodiments, wherein, a tolerance is formed along the radial direction of the telescope between the bracket and the connector.

In some embodiments, at least one glue dispensing groove is arranged on the inner wall of the end of bracket that cooperates with the connector.

In some embodiments, a step portion is arranged on the inner wall of the bracket at the place corresponding to the middle of the output end of the imaging means and the first assembly.

The connector according to the invention connects the parts in the telescope to be an integrated body with a precision location, improves the quality of imaging and simplify the structure of the endoscope.

BRIEF DESCRIPTION OF THE DRAWINGS

The aforementioned features and advantages of the invention as well as additional features and advantages thereof will be more clearly understood hereinafter as a result of a detailed description of embodiments when taken in conjunction with the drawings.

Like reference numerals refer to corresponding parts throughout the multiple views of the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

Figure 1:
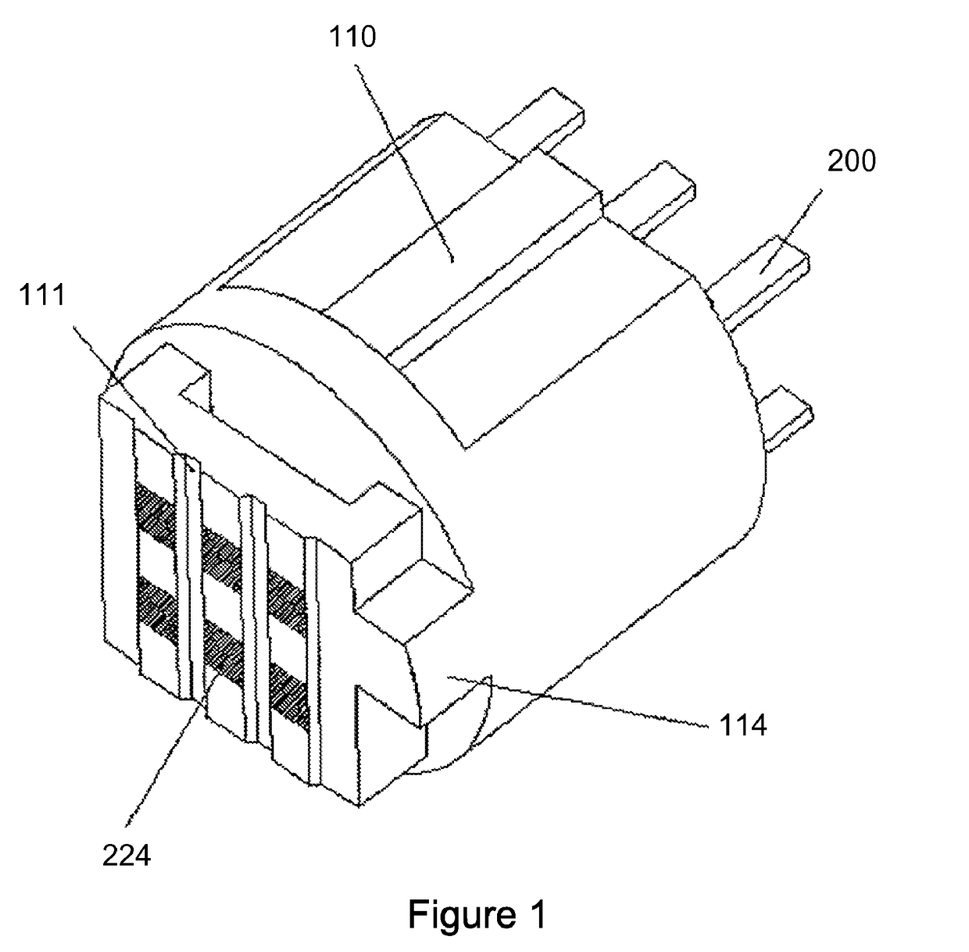
FIG. 1 is a perspective view of the connector according to a first embodiment of the present invention.
Figure 2:
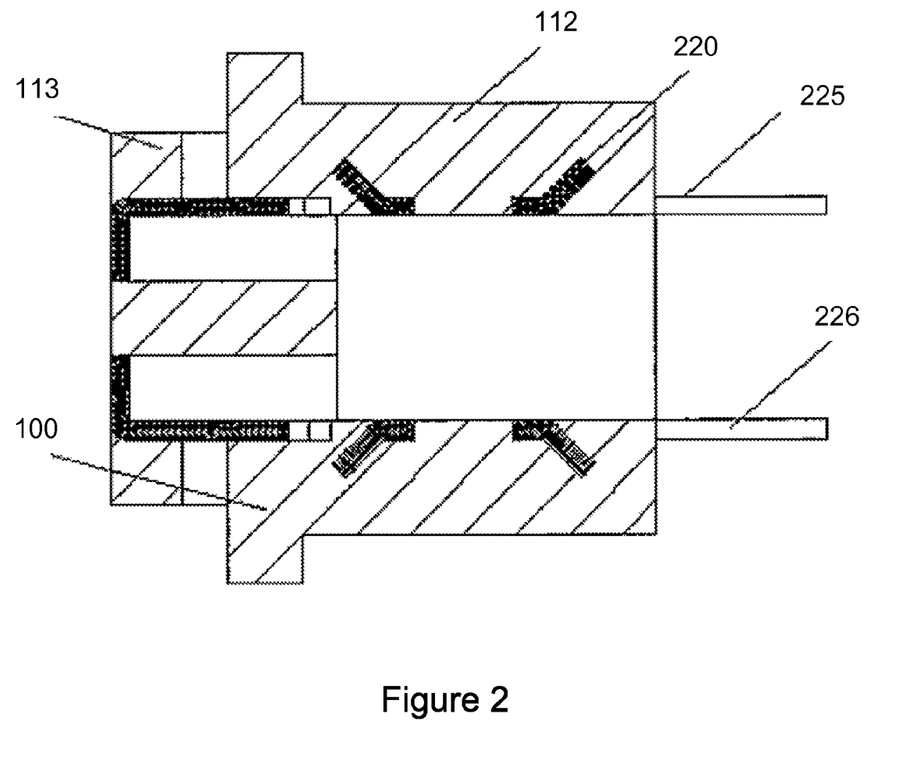
FIG. 2 is a sectional view of the connector of FIG. 1.
Figure 3:
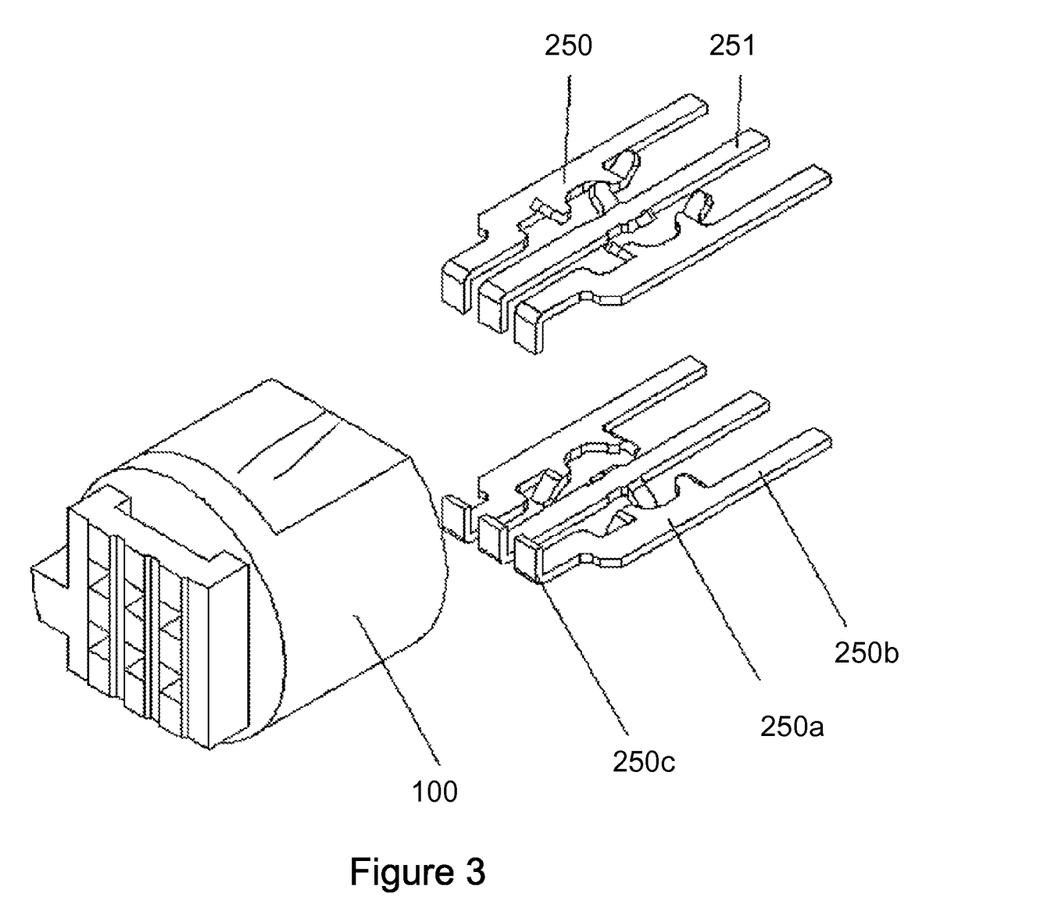
FIG. 3 is an exploded view of the connector of FIG. 1.

FIGS. 1 to 3 illustrate a connector according to a first embodiment of the invention, which is used to receive electric signals within a tubular structure such as an endoscope. As shown in FIGS. 1 to 3, the connector comprises an insulation body 100 and multiple conductive terminals 200 extending from the body 100 that are fixed within the body 100 through insert molding. Insert molding is a method of injecting melted resin into a mould after the ends of the terminals 200 are located into the mould. The resin is cured to fix the terminals and form an integrated product. The holding portions 220 may be formed such that a side of the terminal 200 is bent to form a projection. In some embodiments, each holding portion 220 has its own bending direction to balance the stress in different directions so that the terminals 220 and the body 100 are tightly fixed together. In this embodiment, each terminal 200 has two symmetric holding portions 220, although more than two can be used. Because (i) the connector is formed by insert molding and without the step of assembling the conductive terminals 200 and (ii) the insulation body 100 and the holding portions 220 are formed on the terminal 200, the connection of the terminals 200 within the body 100 is strong. Further, insert molding is also efficient and therefore reduces the production cost, simplifies the manufacturing process, and increases the reliability of the connector.

The conductive terminal 200 comprises a first conductive terminal group 225 and a second conductive terminal group 226 that are oppositely located. Each group comprises two exterior first conductive terminals 250 and a second conductive terminal 251 between the two first conductive terminals 250. Each of the first and second conductive terminals includes a main portion 250a, a contact portion 250b extending from the main portion 250a, and a welding portion 250c with a bent end. The holding portion 220 is located on the main portion 250a. Further, the holding portions 220 of the first terminal 250 are symmetric with reference to the longitudinal axis of the first terminal 250, and the holding portions 220 of the second terminal 251 are symmetric with reference to the transversal axis of the second terminal 251. The holding portions 220 enhance the engagement force between the terminals 200 and the insulation body 100 to tightly fix the terminals 200 within the body 100. A welding pad 224 with one or more guiding grooves 111 is connected to the welding portion 223, and the guiding grooves 111 can guide the welding pad 224 accurately in the course of insert molding to weld related parts.

In some embodiments, the insulation body 100 includes a body portion 113 and a connection portion 112 connecting to the body portion 112. A first projection 110 and a second projection 114 are formed on the insulation body 100 to prevent the connector from being assembled onto other components in a wrong way. The longitudinal axes of the projections may be parallel to the longitudinal axis of the terminals so as to distinguish the direction of the connector while assembling the same with the other components.

The contact portion 250b of the terminal 200 inserts and connects to a printed circuit board (PCB, not shown), and the first projection 110 guides the insertion and connection of the contact portion 250b. The welding portion 250c of the terminal 200 can connect to a sensor (not shown) by welding with the guidance of the guiding grooves 111, and the second projection 114 also guides and locates the welding portion to prevent it from being connected to the sensor inversely.

FIGS. 4 to 9 illustrate a connector according to a second embodiment of the invention. As shown in FIGS. 4 to 9, the connector 5 includes a body 51 and multiple terminals 52 extending from the body 51. The body 51 is formed with the terminals 52 by insert molding. Ends of the terminal 52 are electrically connected to an image sensor 3 and a PCB board 4 of an endoscope. The terminal 52 has a head portion 50 that is flat and a foot portion 522. The top surface of the head portion 50 is exposed at one end face of the body 51 to form an engagement face 513. The foot portion 522 extends from the other end face of the body 51. Multiple extending portions 53 are formed by inclining the foot portion 522 outward to provide the tight connection between the terminal 52 and the body 51.

Figure 4:
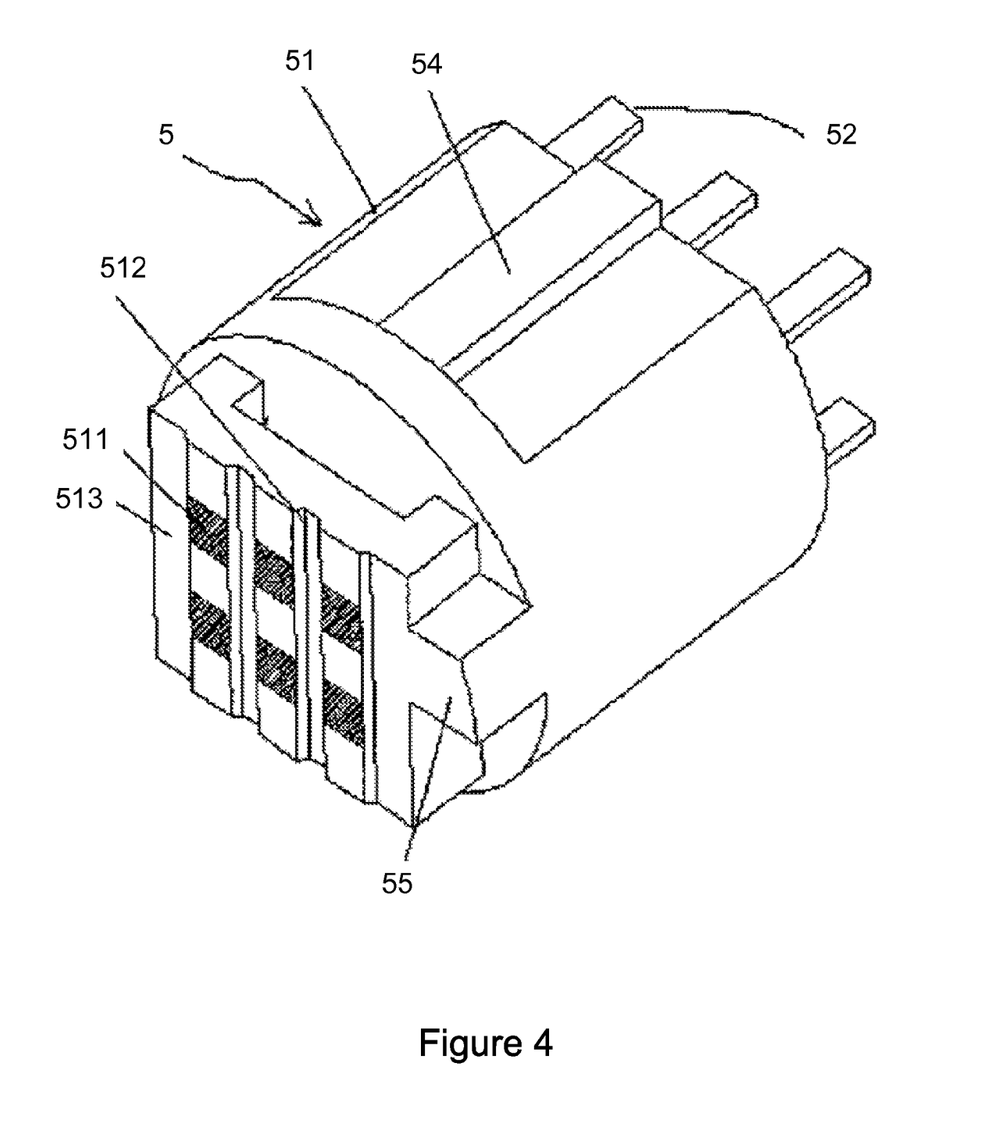
FIG. 4 is a perspective view of the connector according to a second embodiment of the invention.
Figure 5:
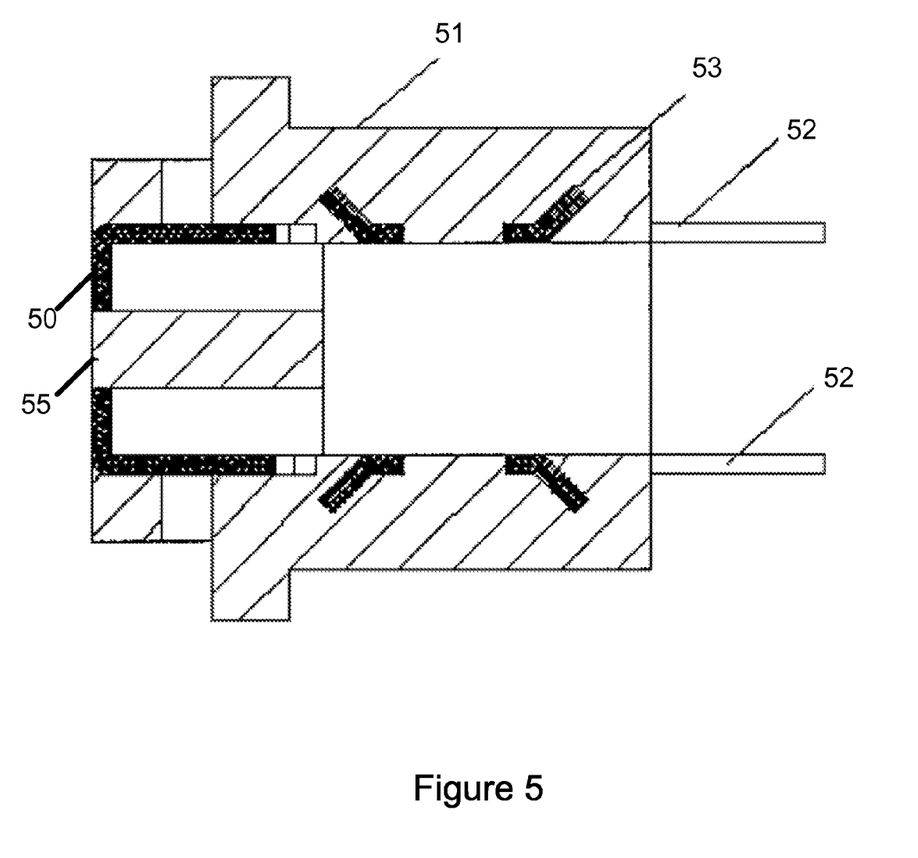
FIG. 5 is a sectional view of the connector of FIG. 4.
Figure 6:
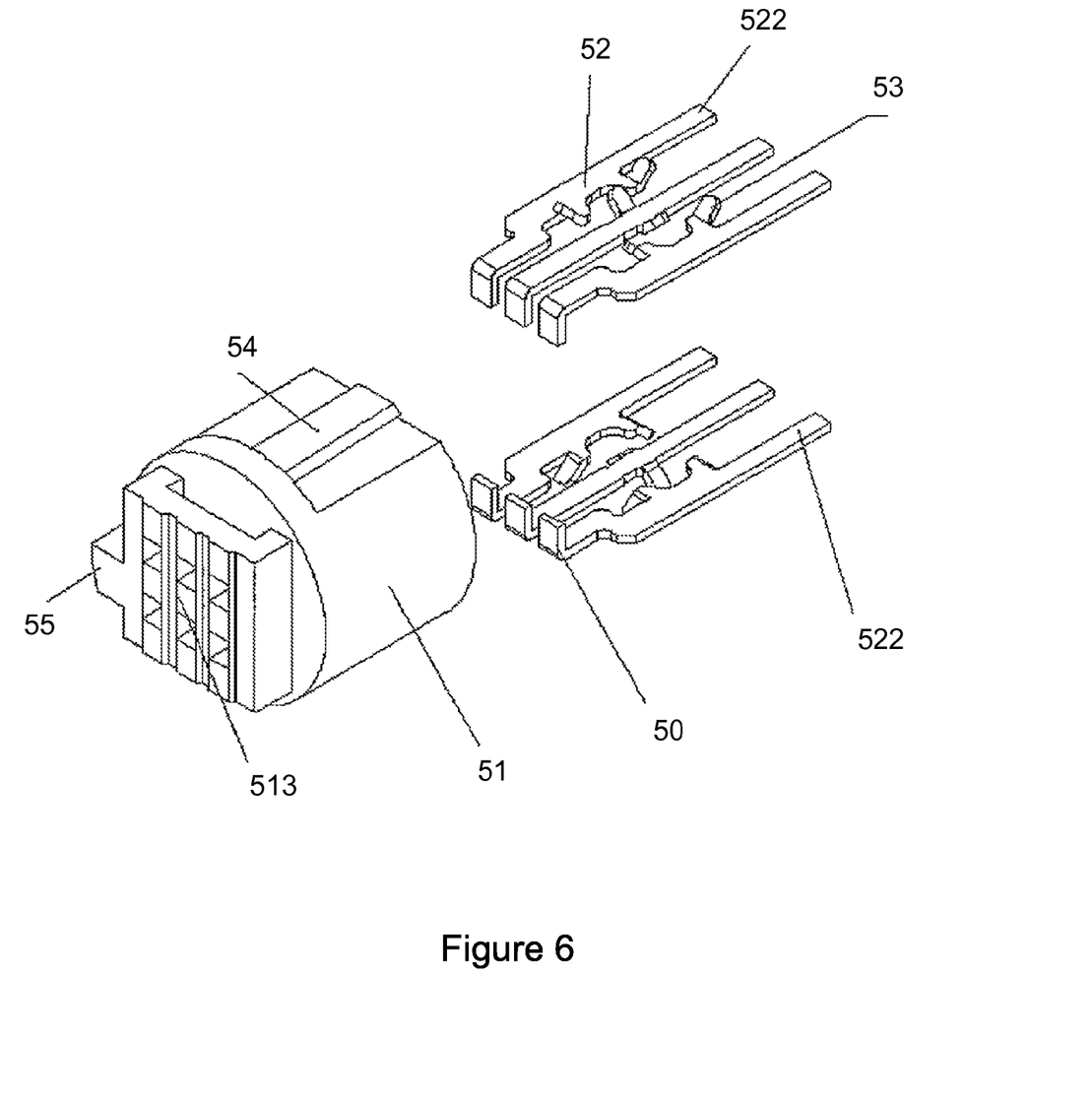
FIG. 6 is an exploded view of the connector of FIG. 4.
Figure 7:
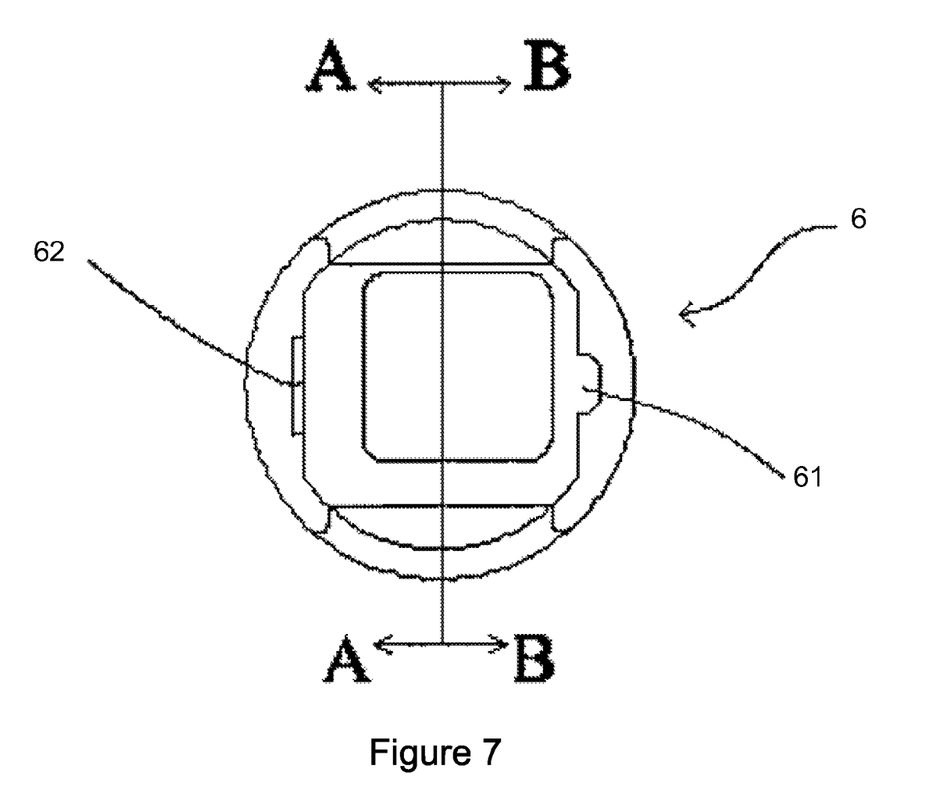
FIG. 7 is a front view of the bracket according to the invention.

A welding pad 511 is connected to the head portion 50 and has at least one guiding groove 512 to precisely locate the welding pad 511 in the course of insert molding.

In some embodiments, the body 51 has a first projection 54 and a second projection 55 whose longitudinal axes may be parallel to the longitudinal axes of the terminals. The projections 54 and 55 can prevent the connector from being improperly assembled onto other components.

The foot portion 522 of the terminal 52 inserts and connects to a PCB board (not shown) with the guidance of the first projection 54. The welding pad 511 of the terminal 52 can connect to a sensor (not shown) by welding with the guidance of the guiding grooves 512, and the second projection 55.

The present invention also discloses a method of manufacturing the connector, which includes the following steps: pressing the material belt to form a conductive terminal; bending and extending one end of the conductive terminal to form a clamping portion; and putting at least one of the conductive terminals so obtained in position within a mould, then folding the mould and insert molding to form a connector having an insulation body and conductive terminals. In the step of pressing the material belt to form a conductive terminal, two or more clamping portions having different bending directions are formed.

Figure 10:
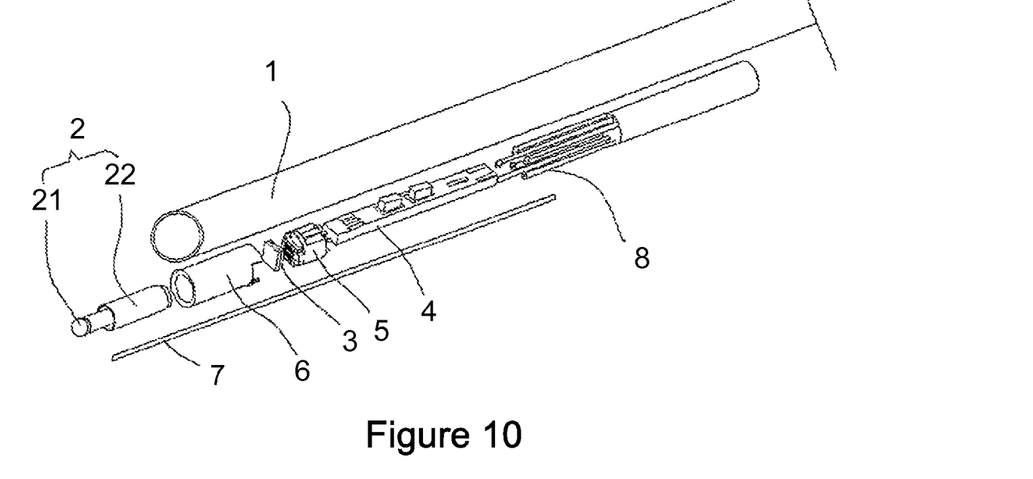
FIG. 10 is an exploded view of an endoscope according to an embodiment of the present invention.
Figure 11:
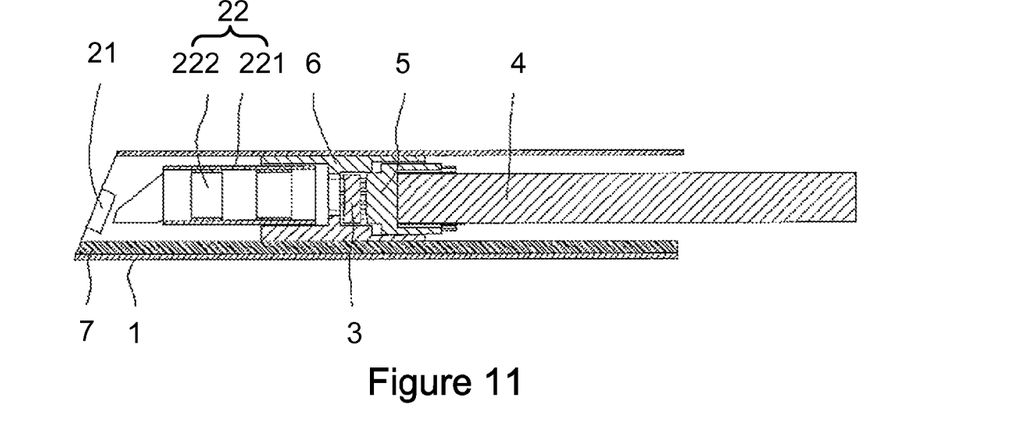
FIG. 11 is a sectional view of the endoscope of FIG. 10.

FIGS. 10 and 11 illustrate an endoscope according to another example of the invention. As shown in FIGS. 10 and 11, the endoscope includes a telescope 1, an imaging means 2, an image sensor 3 such as a CCD image sensor that converts the optical images from the imaging means 2 to electronic signals, and a PCB board 4 that organizes and outputs the electronic signals. The imaging means 2 includes a group of lens, and the imaging means 2, image sensor 3 and the PCB board 4 are located in the telescope 1. The endoscope further includes a connector 5, such as the aforementioned connectors with reference to FIGS. 1 to 3 and a clamping bracket 6. The image sensor 3 and the PCB board 4 are connected together as a first assembly by the connector 5. One end of the bracket 6 connects to the output end of the imaging means 2 to form a second assembly, and another end of the bracket is fixed to the first assembly so as to integrate the first and second assemblies. The bracket 6 can be tubular. Therefore, the components in the telescope 1 are integrated together via the connector 5 and the bracket 6 as a simple structure with a precise location to provide high quality images.

The imaging means 2 includes a lens 21 and a lens group 22 located at the front end of the telescope 1. The output end of the imaging means 2 is connected to one end of the bracket 6 via glue dots. The lens group 22 includes a tube 221 and multiple lenses 222 within the tube 221. The front end of the bracket 6 partially surrounds the outer wall of the tube 221 along the axial direction of the telescope 1. Because there is a focus tolerance up to 1 mm between the lens group 22 and the image sensor 3 when the optical signals are transmitted, the location of the lens group 222 relative to the image sensor 3 can be axially adjusted during the course of mounting the tube 221 to the bracket 6 via glue dots to adjust the focus. In some embodiments, the bracket surrounds the entire tube 221 along the axial direction of the telescope 1 or the bracket 6 may surround multiple lenses 222 without using the tube 221. In this case, focus is adjusted by adjusting the image sensor 3 under this situation.

Optical fiber 7 is attached to the inner wall of the telescope 1 via glue. The optical fiber 7 illuminates the area around the lens 21 via an outside source for taking pictures by the lens 21.

While assembling the first assembly, the image sensor 3 and the engagement face 513 of the connector 5 are coupled together by surface mounted technology (SMT) so as to form an electrical connection to the head portion 50 of the terminal 52. The output end of the PCB board 4 is electrically connected to the foot portion 522 of the terminal 52.

As shown in FIG. 4, a bar-like projection 54 is formed on the outer wall of the body 51 of the connector 5 along the axial direction of the telescope 1 for the convenient engagement between the connector 5 and the bracket 6. Since the image sensor 4 and the PCB board 4 connecting to the connector 5 have an orientation, the projection 5 can guide the operators to assemble the image sensor 3 and the PCB board 4 properly.

Figure 8:
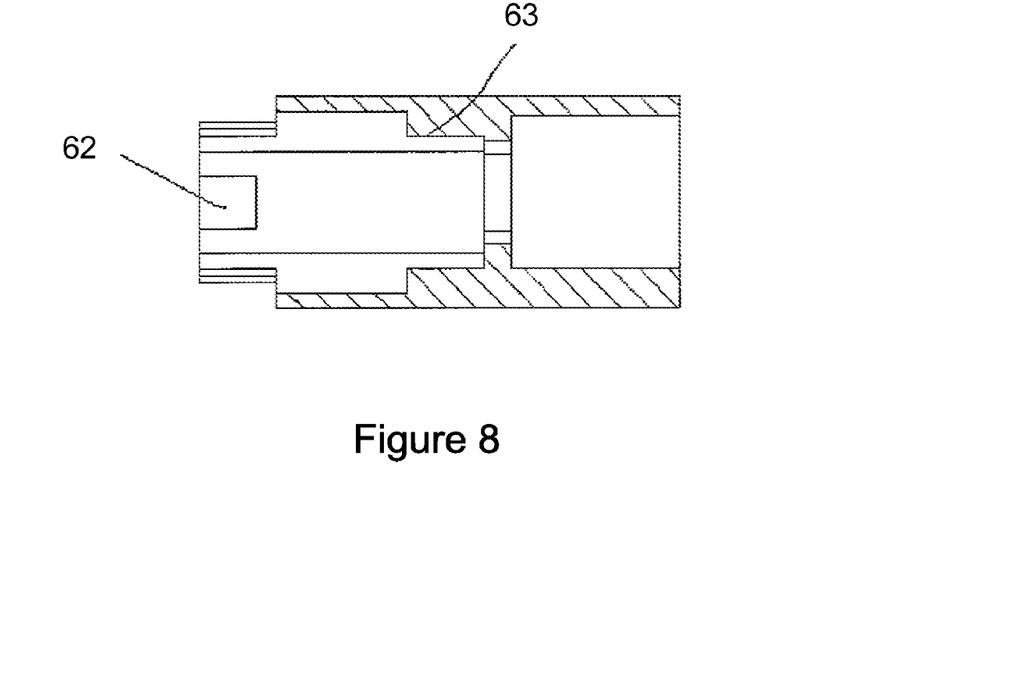
FIG. 8 is a cross-sectional view along line A-A of FIG. 7.
Figure 9:
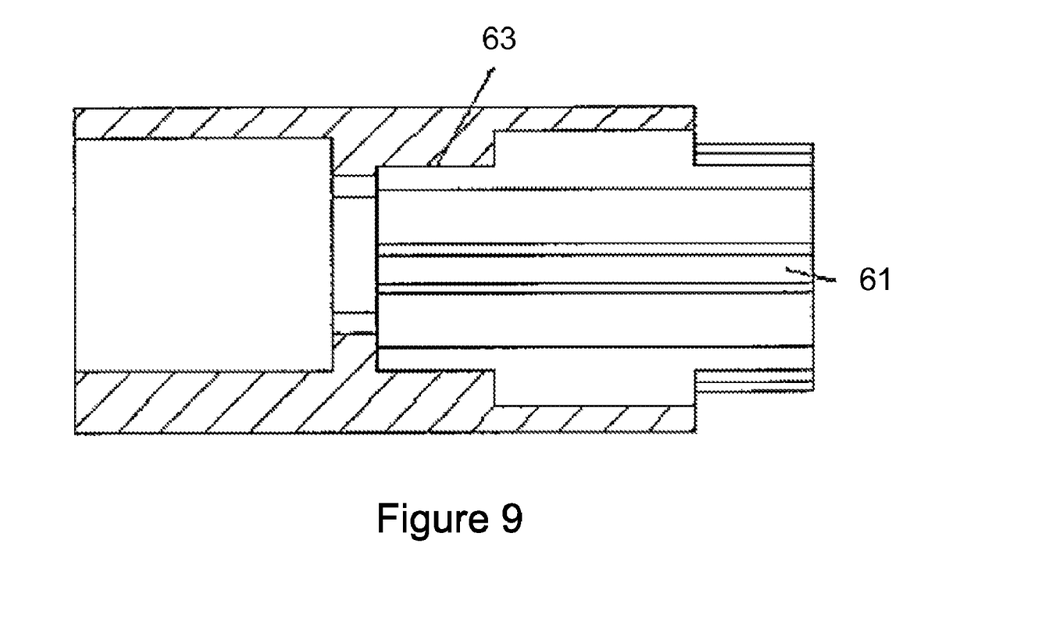
FIG. 9 is a cross-sectional view along line B-B of FIG. 7.

As shown in FIGS. 8 and 9, the bracket 6 is tubular, with one end being fixed at the output end of the imaging means 2 and the other end surrounding and being fixed at the connector 5. A groove 61 is formed in the inner wall of the bracket 69 to match the projection 54 of the connector 5. When the connector 5 is fixed onto the bracket 6, the projection 54 inserts into the groove 61. Note that the locations of the groove 61 and the projection 54 form a projection-groove configuration on the connector 5 and bracket 6. For instance, the projection 54 can be formed on the inner wall of the bracket 6 and the groove 61 can be formed in the outer wall of the connector 5.

In some embodiments, a glue dot groove 62 is formed on the inner wall at the end of the bracket 6 that works in concert with the connector 5 to control the glue amount used to connect the connector 5 and the bracket 6. In one embodiment, there is a tolerance between the bracket 6 and connector 5 along the radial direction of the telescope 1 at the end of bracket 6. By fixing the connector 5 and bracket 6 using glue, the focus can be adjusted by radially adjusting the relative position of the connector 5 to the bracket 6. Further, a step portion 63 is formed on the inner wall of the bracket 6 at a position corresponding to the position between the output end of the imaging means 2 and the first assembly to strengthen the bracket 6.

Signals are transmitted as shown in FIG. 11. An image produced by the lens 21 is transmitted by the lens group 22 to the sensitive area of the image sensor 3, which converts the image into electrical signals and outputs he signals to the PCB board 4 for filtering. The filtered electrical signals are transmitted to another PCB board (not shown) via a digital cable 8 and are displayed as a final picture on a display means (now shown).

The invention also provides a method to make the endoscope that includes the following steps: connecting the image sensor 3 and the PCB board 4 via the connector 5 to form the first assembly; connecting an end of the bracket 6 to the output end of the imaging means 2 to form the second assembly; connecting the other end of the bracket 6 to the first assembly to integrate the first and second assemblies; locating optical fiber 7 on the inner wall of the telescope 1 and fixing the same via glue dots; and putting the integrated first and second assemblies into the telescope 1 having the optical fiber 7 and fixing the same with glue dots. In some embodiments, the optical fiber 7 can be heat treated to withstand the heat load brought by the outside light source and to become expansible to have the components in the telescope 1 connected more tightly.

When connecting the imaging means 2 and the bracket 6 or connecting the first assembly and the bracket 6, the focus is adjusted before fixing the relative components. The focus adjustment can be done by axially adjusting the relative position between the imaging means 2 and the bracket 6, by radially adjusting the relative position between the bracket 6 and the first assembly, or by simultaneously adjusting the imaging means 2 and the relative position between the first assembly and the bracket 6.

According to this method, the connector 5 and the bracket 6 integrate the components in the telescope 1 into one body to position them precisely, improve the image quality, and simplify the manufacturing method.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An electrical connector for use in an endoscope, comprising:
   an elongated insulation body having a longitudinal axis and including a matrix of welding pads divided by a plurality of parallel guiding grooves located at an end surface that is substantially perpendicular to the longitudinal axis; and
   a plurality of conductive terminals that are permanently fixed within the elongated insulation body, substantially parallel to the longitudinal axis of the elongated insulation body, and electrically insulated from one another, wherein each conductive terminal includes a head that is bent to be electrically coupled to one of the matrix of welding pads, a pair of clamping fins that are projected into the elongated insulation body in respective directions that are substantially deviated from the longitudinal axis of the elongated insulation body, and a tail that is located outside the elongated insulation body substantially along the longitudinal axis of the elongated insulation body.

2. The electrical connector according to claim 1, wherein the respective directions of the pair of clamping fins define a plane that is substantially perpendicular to the longitudinal axis of the elongated insulation body.

3. The electrical connector according to claim 1, wherein the respective directions of the pair of clamping fins define a plane that is substantially parallel to the longitudinal axis of the elongated insulation body.

4. The electrical connector according to claim 1, wherein the plurality of conductive terminals are divided into a first group and a second group, and the first group of conductive terminals is symmetric to the second group of conductive terminals with respect to the longitudinal axis of the elongated insulation body.

5. The electrical connector according to claim 4, wherein each of the first and second groups includes at least three conductive terminals.

6. The electrical connector according to claim 4, wherein the heads of the first group of conductive terminals are bent in a first direction within the end surface of the elongated insulation body and the heads of the second group of conductive terminals are bent in a second direction opposite the first direction within the end surface of the elongated insulation body.

7. The electrical connector according to claim 1, wherein the elongated insulation body is formed by injecting melted resin into a mould after the plurality of conductive terminals have been placed into the mould.

8. The electrical connector according to claim 1, wherein there are a first elongated ridge and a second elongated ridge at an outer wall of the elongated insulation body.

9. The electrical connector according to claim 8, wherein the first elongated ridge and the second elongated ridge are substantially parallel to the longitudinal axis of the elongated insulation body.

10. The electrical connector according to claim 8, wherein the first elongated ridge and the second elongated ridge are located at two different sides of the outer wall of the elongated insulation body that are substantially perpendicular to each other.

11. The electrical connector according to claim 8, wherein the first elongated ridge is located remote from the end surface of the elongated insulation body to engage an inner groove of a bracket that houses the electrical connector.

12. The electrical connector according to claim 8, wherein the first elongated ridge is located remote from the end surface of the elongated insulation body to guide the engagement of the plurality of conductive terminals with a printed circuit board external to the electrical connector.

13. The electrical connector according to claim 8, wherein the second elongated ridge is located near the end surface of the elongated insulation body to guide the engagement of the matrix of welding pads with an image sensor external to the electrical connector.

14. The electrical connector according to claim 1, wherein there is a cavity defined an inner wall and the end surface of the elongated insulation body.

\* \* \* \* \*